United States Patent [19]

Steel et al.

[11] Patent Number: 4,797,552
[45] Date of Patent: Jan. 10, 1989

[54] APPARATUS AND METHOD FOR LOCATING THE DIRECTION OF AN ATOMIC BEAM

[75] Inventors: Duncan G. Steel, Ann Arbor, Mich.; R. Steven Turley, Newbury Park, Calif.

[73] Assignee: Hughes Aircraft Company, Los Angeles, Calif.

[21] Appl. No.: 23,844

[22] Filed: Mar. 9, 1987

[51] Int. Cl.[4] .............................................. H01S 1/00
[52] U.S. Cl. ................................. 250/251; 356/138; 356/150; 324/71.3
[58] Field of Search ............................ 250/251, 458.1; 356/121, 138, 150, 152, 375, 400

[56] References Cited

PUBLICATIONS

Applied Phys. Lett., vol. 39, No. 9, Nov. 1, 1981, Am. Inst. Phys. (US), J. L. Hall et al.: Optical Heterodyne Saturation Spectroscopy, pp. 680-682, see abstract; FIG. 1.
Rev. of Sci. Instr., vol. 15, No. 1, Jan. 1985, Am. Inst. Phys. (US), M. J. Verheijen et al: Accurate (0.25 mrad), Perpendicular Alignment of a Continuous-Wave Single-Mode Dye Laser Beam and an Atomic Beam, pp. 62-65, see abstract: "Introduction", FIGS. 1, 4.
Jour. of Phys. E. Sci. Instr., vol. 15, No. 11, Nov. 1982, M. J. Verheijen et al., An Atomic-Beam Set-Up for 0.5 MHz Absolute Frequency Stabilization of a Single-Mode CW Dye Laser, pp. 1198-1206, see abstract; FIGS. 2, 3, 4.
Optics Lett., vol. 5, No. 1, Jan. 1980, Op. Soc. of Am. (US), G. C. Bjorklund: Frequency-Modulation Spectroscopy: A New Method for Measuring Weak Absorptions and Dispersions, pp. 15-17, see p. 15, left-hand col., lines 1-10, FIG. 1.

Primary Examiner—Carolyn E. Fields
Assistant Examiner—John A. Miller
Attorney, Agent, or Firm—Wanda K. Denson-Low; A. W. Karambelas

[57] ABSTRACT

Related systems and methods are described for determining the angular direction of an atomic beam relative to the beam's reference axis. For a non-relativistic atomic beam, a pair of counterpropagating, equal frequency laser beams intersect the atomic beam at a known angle to the reference axis, preferably perpendicular. The atomic beam direction is inferred from the frequency difference between resonant peaks in the laser beam fluorescence as the laser frequency is scanned. For a relativistic atomic beam, a pair of laser beams intersect the atomic beam from different sides at equal predetermined angles. The atomic beam direction is determined by observing the difference between resonant absorption peaks in the transmitted laser beam intensities as either the laser beam frequencies or laser beam angles relative to the atomic beam are varied. The angles between the laser and atomic beams are preferably selected to minimize the widths of the resonant peaks. For both the relativistic and non-relativistic cases, an FM derivative spectroscopy technique is used by which the derivatives of the laser beam intensity signals are obtained, and zero crossings of the derivative signal used to precisely locate the resonant intensity peaks.

22 Claims, 5 Drawing Sheets

APPARATUS AND METHOD FOR LOCATING THE DIRECTION OF AN ATOMIC BEAM

BACKGROUND OF THE INVENTION

1. Field of the Invention

This invention relates to the directional location of atomic beams, and more particularly to the use of laser beams in the directional location process.

2. Description of the Related Art

It is often necessary to be able to precisely measure the direction of an atomic particle beam, both in the laboratory and other environments. The necessary directional measurement has heretofore been accomplished by sensing the edges of the beam with a quadrant detector, or by inserting a sensing wire in the beam path. A major problem with such measurement techniques, however, is that they interfere with the beam itself, removing atoms from the beam in the process of accomplishing their sensing function. Also, since they actually sense only a small portion of the beam, they operate upon the assumption that the beam will have a given density profile; this assumption may not be totally accurate and can lead to errors. Furthermore, it would be desirable to increase the accuracy of such measurements systems down to the area of 0.1 microradians.

While not directed toward the measurement of beam direction, a recently published article discusses the attainment of an accurate perpendicular alignment between a laser beam and an atomic beam, M. J. Verheijen, H. C. W. Biejerinck, N. F. Verster, "Accurate (0.25 mrad) Perpendicular Alignment of a Continuous-Wave Single-Mode Dye Laser Beam and an Atomic Beam", Review of Scientific Instruments 56(1), January, 1985, pages 62–65. The article discusses the desirability of Doppler-free observations in several types of crossed laser beam-atomic beam experiments, such as observations of the interactions between atoms and photons, state selection or state sensitive detection of the atomic beam, and collision experiments with atoms that are excited by laser beam.

To achieve the desired perpendicularity between the atomic beam and laser beam, the Verheijen article proposes that two anti-parallel (counterpropagating) laser beams of the same frequency be directed through the atomic beam at right angles to the assumed atomic beam axis; the counter-propagating laser beams may be formed by appropriate optical treatment of a beam from a single laser. An indication of misalignment from perpendicularity is obtained for the actual atomic beam direction by first running a single laser beam through the atomic beam, varying the frequency of the single laser beam, measuring the intensity of the laser beam by sensing its fluorescence out of the plane of the laser and atomic beams for each of a number of different frequencies, and performing a computer calculation to determine the centroid of the fluorescence distribution as a function of frequency. A similar process is then followed with the pair of counterpropagating laser beams: the centroid of the excitation profile for the counterpropagating beams as a function of frequency is computer calculated over the same frequency range as with the single laser beam. The centroids of the single and double laser beam profiles are then compared, with any misalignment between the two indicating a variance from perpendicularity between the laser and atomic beams. The angle between the laser beams and atomic beam is then varied by scanning the atomic beam collimator with a stepper motor parallel to the laser beams and perpendicular to the atomic beam, and the centroid positions with one and two laser beams are recalculated at each different atomic beam angle. The position of the atomic beam collimator at which the difference between the centroids equals zero corresponds to accurate perpendicularity between the laser and atomic beams.

While the Verheijen, et al. article discloses an improved technique for aligning a laser beam to an atomic beam, there is no disclosure of a mechanism for determining the aboslute direction of the atomic beam relative to a reference axis. Also, the article involves a computer calculation at several steps in the process of determining the relative alignment between the laser and atomic beams, whereas it would be desirable to have a real-time monitoring of the actual atomic beam direction without the necessity of performing centroid calculations. Furthermore, the Verheijen, et al. approach requires the use of counterpropagating laser beams close to perpendicular to the atomic beams, at which angle there is a second order Doppler broadening of the fluorescence distribution which is significant in relativistic beams.

SUMMARY OF THE INVENTION

In view of the above problems associated with related art, an object of the present invention is the provision of a novel and improved system and method for measuring the direction of an atomic beam with greater accuracy than previously obtainable, and without interfering with the beam itself.

Other objects are the provision of such a system and method which permits a real-time monitoring of the atomic beam direction, which significantly reduces second order Doppler effects, and which is applicable to both relativistic and non-relativistic beams.

These and other objects of the invention are achieved with a system and method in which a pair of laser beams having a common frequency intersect the atomic beam at known angles to a reference beam axis from different sides of the beam. The laser beam intensities are sensed as either their frequencies or angles relative to the atomic beam are varied, and the intensities are observed to peak at resonant points with the atomic beam. The interval between intensity peaks, with respect to the varying laser beam characteristic, is measured. This interval is an indication of the angular deviation between the atomic beam and the laser beams, and thus of the angular deviation between the actual and reference atomic beam axes. This interval is preferably determined by obtaining the derivatives of the sensed laser beam intensities, and measuring the interval between the derivatives crossing zero.

One embodiment is intended for non-relativistic atomic beams, in which the atomic velocities are substantially less than the speed of light. In this regime relativistic effects do not materially influence the measurement. The laser beams are provided as counterpropagating beams; there is no significant Doppler shift for velocity components perpendicular to the laser beam axis. The laser beam frequency is varied as the beams are directed at substantially right angles to the reference atomic beam axis, and the combined laser beam intensity is sensed by a fluorescence detector positioned out of the plane of the atomic and laser beams.

In another embodiment, intended for relativisitic atomic beams, the laser beam intensities are sensed individually as either the laser beam frequencies or angles are varied. The interval between absorption peaks in the transmitted laser beam intensities is measured. In either case the laser beams are centered on an angle to the atomic beam which minimizes the spread of the intensity profiles. The derivative signal is obtained by an FM spectroscopy technique in which a radio frequency sweep signal generator and an electro-optic modulator apply a radio frequency modulation to the laser beams before they reach the atomic beam; the output of the laser beam intensity sensors are then demodulated to yield a DC derivative signal. When the laser beam angles rather than frequencies are varied, a lens is positioned in front of a photodetector used to sense the intensity of each laser beam, to accommodate the angular variations in the laser beams.

The invention provides a highly accurate real-time technique for measuring the atomic beam direction. These and other objects and features of the invention will be apparent to those skilled in the art from the following detailed description of preferred embodiments, taken together with the accompanying drawings, in which:

DETAILED DESCRIPTION OF PREFERRED EMBODIMENTS

The present invention may be applied to determine the direction of both relativistic and non-relativistic atomic beams. A system intended to be used with a non-relativistic beam is illustrated in block diagram form in FIG. 1. An atomic beam 2 is indicated as being directed along an axis which is at a slight angle to a reference beam axis 4, otherwise referred to as the boresight. In actual practice the angular divergence between the actual beam 2 and its reference axis 4 will typically be up to a few degrees; the divergence is exaggerated in FIG. 1 for purposes of illustration. (For relativistic beams, the divergence is typically on the order of microradians to milliradians).

Figure 1:
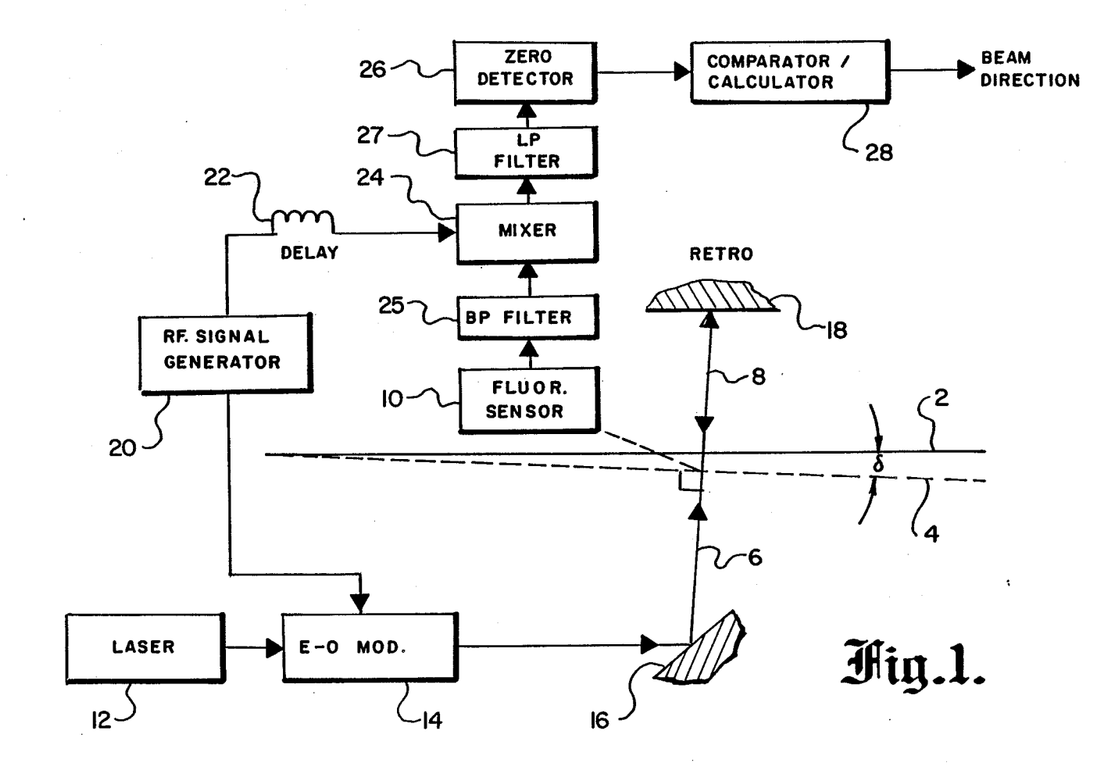
FIG. 1 is a block diagram of one embodiment of the invention, intended to measure the direction of a non-relativistic atomic beam.

A pair of counterpropagating (anti-parallel) laser beams 6 and 8 are directed through the atomic beam at a right angle to the reference axis 4. The laser beams have a common frequency which is selected so that the beams resonate at an atomic energy transition level of the atomic beam. The intensity of the laser beams is sensed by a fluorescence sensor 10, which detects the level of light scattered from the beams; sensor 10 is located out of the plane of the atomic and laser beams. For example, the intensity of a sodium beam can be sensed via the transition from level 3s to level 3p at a wavelength of 589.0 nm.

While the two laser beams 6 and 8 can be generated separately, they are preferably produced by a single, frequency tunable laser 12, which has a base frequency at an atomic resonance frequency of the atomic beam. The laser output is passed through an electro-optical modulator 14 where it receives a radio frequency modulation, as explained further below, and is then reflected off mirror 16 and through the atomic beam at the desired right angle to the reference atomic beam axis 4. A retroreflective mirror 18 is positioned in the laser beam path on the opposite side of the atomic beam, and reflects the laser beam 6 back along the same path as counterpropagating beam 8. The counterpropagating beams can be achieved by ensuring overlap of the two beam spots on an optical surface at a sufficient distance from retro-reflector 18 to provide sufficient angular resolution.

A radio frequency signal generator 20 generates an rf signal which is applied to the electro-optic modulator 14 to impress a phase modulation onto the laser beams. The rf signal is also delivered through a delay circuit 22 to a mixer 24, which receives a second input representing the filtered laser beam intensity from the fluorescence sensor 10. A band pass filter 25 is provided to pass only those components of the output of sensor 10 which are at the frequency of the rf generator 20. The delay circuit 22 is selected to bring the two inputs to mixer 24 into phase; it could also be provided at the output of fluorescence sensor 10, rather than the output of rf signal generator 20.

Mixer 24 is a commercially available device, such as Avantek, Inc. model DBX-184H or Mini Circuits, Inc. model ZAD-11H. It demodulates the laser intensity signal and produces an output which is integrated to a DC signal by a low pass filter 27. The output of low pass filter 27 is proportional to the amplitude of the sum of the two sideband components of the input signal from fluorescence sensor 10. The output is the derivative of the fluorescence signal from filtered sensor 10 as a function of laser beam frequency, over the tunable frequency range. This technique of obtaining the derivative (slope) of a spectral output by modulating the frequency of an input laser beam is referred to as Frequency Modulated Derivative Spectroscopy (FMDS). The general FMDS technique is disclosed in an article by G.C. Bjorklund, "Frequency Modulation Spectroscopy: A New Method for Measuring Weak Absorptions and Dispersions", Optics Letters 5, 15 (1980), and in J. L. Hall, H. T. Baer and H. G. Robinson, "Optical Heterodyne Saturation Spectroscopy", Applied Physics Letters 39, 680 (1981); the contents of both articles are incorporated herein by reference.

The mixer output is applied to a zero detection circuit 26, which senses when the derivative signal has gone through zero. The output of zero detector 26 is forwarded to a comparator/calculator circuit 28 which compares the frequency-separated zero derivative points, as explained below, to calculate the actual beam direction.

Figures 2, 3:
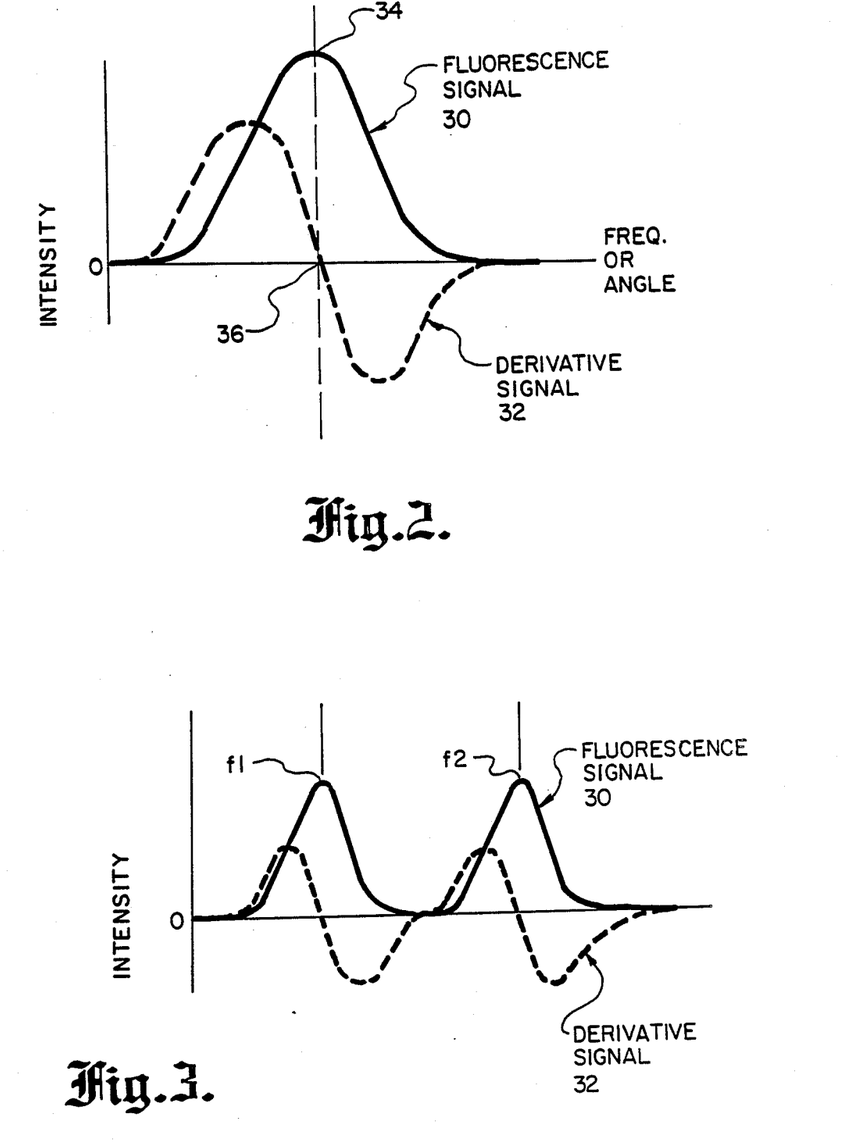
FIG. 2 is a graph of the laser beam intensity with the system of FIG. 1 over a portion of the laser frequency spectrum, and of the derivative of the intensity signal.
FIG. 3 is a graph of the laser beam intensity with the system of FIG. 1 over a larger portion of the laser frequency spectrum, and the derivative thereof, illustrating the manner in which the atomic beam direction can be obtained from the laser beam intensity profile.

FIG. 2 is a graph illustrating the DC component of the fluorescence signal 30 produced by fluorescence sensor 10 over a portion of the tuneable frequency spectrum of laser 12. The corresponding derivative signal output from filter 25 is illustrated by dashed curve 32. It can be seen that, when the fluorescence signal 30 is at a peak 34, the derivative signal 32 passes through a zero point 36. Fluorescence peak 34 occurs when one or the other of the laser beams 6, 8 is in resonance with an energy transition of the atomic beam. This phenomenon is employed to accurately determine the beam direction.

Variations in the fluorescence signal 30 and in the derivative signal 32 over the full laser frequency range are illustrated in FIG. 3. The intensity profile will be discussed in conjunction with the atomic beam orientation illustrated in FIG. 1. When the atomic beam 2 is at a non-zero angle to its reference axis 4, the counter-propagating laser beams 6 and 8, which are perpendicular to the reference axis 4, will be offset from perpendicular to the atomic beam. This produces a Doppler shift, since laser beam 6 has a directional component in the same direction as atomic beam 2, and laser beam 8 has a directional component opposite to the atomic beam direction. Thus, the laser beams will establish a resonance with the atomic beam at two different frequencies $f_1$ and $f_2$, with the interval between the two resonant frequencies corresponding to the offset $\delta$ from perpendicular between the laser and atomic beams. For large offsets, the offset angle $\delta$ is related to the frequency interval between intensity peaks by the expression $$f_2 - f_1 = kv(\sin\delta)/\pi$$

where k is equal to $2\pi$ divided by the laser wavelength, and v is the atomic beam velocity.

For small offsets, the formula for the offset angle $\delta$ becomes more complicated and depends on the line shape of the fluorescence spectrum. For homogeneous broadening (with a Lorentzian line shape) the expression for $f_2 - f_1$ is replaced by $$f_2 - f_1 = 2[\Delta(4\Delta^2 + \Gamma^2)^{\frac{1}{2}} - (\Delta^2 + \Gamma^2/4)]^{\frac{1}{2}}$$

where $\Delta = kv (\sin \delta)/2\pi$. $\Gamma$ is the full width at half maximum of the Lorentzian fluorescence line shape. For $\Delta$ less than $\Gamma/2\sqrt{3}$, the combined fluorescence will have only one peak. For inhomogeneous broadening (with a Gaussian line shape) the expression for $f_2 - f_1$ is replaced by $$f_2 - f_1 = 2\nu,$$

where $$\nu = \Delta \tanh(\Delta\nu/\sigma^2)$$

where $\sigma$ is the root mean square width of the gaussian distribution. These calculations are carried out by the comparator/calculator circuit 28. For $\Delta$ less than $\sigma$, only one peak will appear in the fluorescence spectrum.

It is important that the two laser beams, 6 and 8, be precisely counter-propagating and perpendicular to reference axis 4. This can be established by looking for symmetric interferometric fringes from the small amount of light transmitted through mirror 16 or 18. The perpendicularity of the counter-propagating beams with the reference axis can also be established interferometrically.

The intensity peaks at $f_1$ and $f_2$ are reached gradually rather than abruptly, so there can be an error in trying to determine the exact location of each peak. This error is largely removed by obtaining the derivative signal 32. Rather than having to center on a peak, with the derivative signal one can look for a zero crossing of the derivative to determine the frequency of the intensity peak; a zero crossing can be determined more accurately than a direct measurement of the peak.

Since the angular deviation $\delta$ between the laser beams and a perpendicular to the reference atomic beam axis 4 can be determined from the above expression, the angular deviation of the actual atomic beam from its reference axis will also be known, thus providing directional information for the acutal beam. The distance between the peak frequencies $f_1$ and $f_2$ will increase as the atomic beam diverges from its reference axis; the two peaks will merge as the atomic beam approaches its reference axis. With the described system an angular resolution of about 0.3 microradians can be achieved. While useable results can be obtained by setting the laser beams at an angle other than perpendicular to the reference atomic beam axis and adjusting for the resulting built-in Doppler effect, the greatest accuracy is obtained with the laser beams at right angles to the reference atomic beam axis.

The FM derivative technique produces a modulated laser signal that has side bands which are 180° out of phase (see the article by Hall, et al. mentioned above). The two side bands will be absorbed differently in the atomic beam, depending on how far the carrier signal is from the center of resonance. If the carrier is exactly on resonance, the two side bands will be absorbed equally. If the carrier is to one side of the resonance, one side band will be absorbed more than the other, and the net beat signal from the side bands beating against the carrier will be non-zero. Whether the carrier is above or below resonance can be determined from the phase of the rf beat signal. Unambiguous information about the direction of the atomic beam's angular deviation from its reference axis is thereby provided by the sign of the error signal.

The system described above is applicable only to non-relativistic atomic beams. Its sensitivity will be reduced if there is a spread in atomic velocities within the atomic beam, or if the average beam velocity fluctuates over time. With a relativistic beam, which has a velocity that is appreciable compared to the speed of light, there will be a Doppler shift of the atomic resonance frequency even if the laser beam is exactly perpendicular to the atomic beam.

Figure 4:
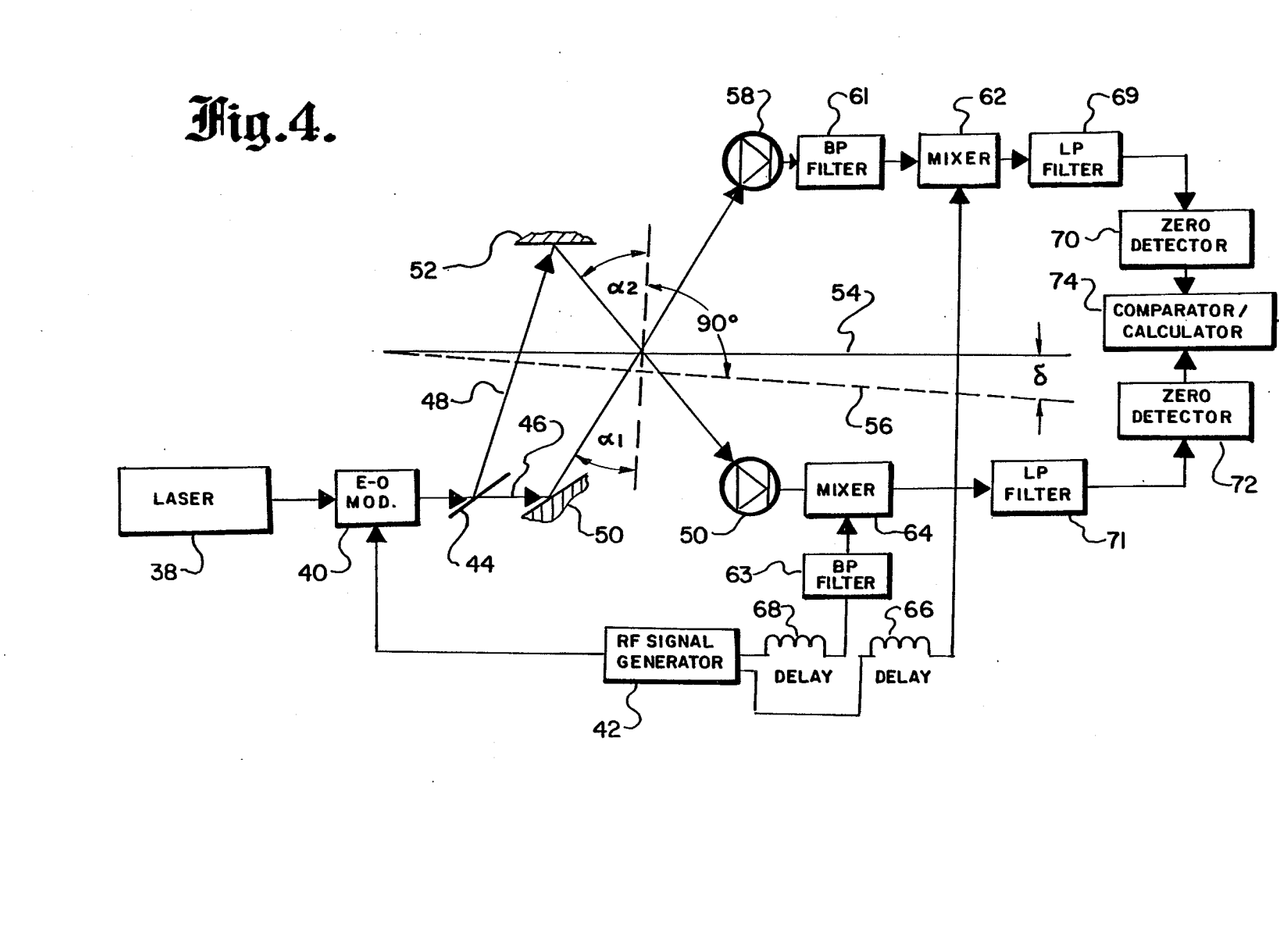
FIG. 4 is a block diagram of another embodiment of the invention intended for use with relativistic beams.

A system which has been developed to determine the direction of a relativistic atomic beam, and which is much less sensitive to changes in atomic beam velocity either over time or across the beam profile, is illustrated in FIG. 4. It uses a tunable laser 38 similar to the laser 12 of FIG. 1. The laser beam is directed through an electro-optic modulator 40, where it receives a phase modulation from radio frequency generator 42. The modulated laser beam emerging from modulator 40 is divided by a beam splitter 44, with the two resulting laser beams 46 and 48 directed respectively to mirrors 50 and 52 on opposite sides of the relativistic atomic beam 54. The two laser beams 46 and 48 are reflected on intersecting paths through the atomic beam at angles $\alpha_1$ and $\alpha_2$ to a perpendicular of the reference atomic beam axis 56. Photodiode detectors 58 and 60 detect the intensities of laser beams 46 and 48, respectively, after transmission through the atomic beam. The output signals from photodetectors 58 and 60 are delivered through band pass filters 61 and 63 to mixers 62 and 64, respectively, which also receive inputs from the rf signal generator 42 through delay lines 66 and 68, respectively. Low pass filters 69 and 71 are provided at the outputs of mixers 62 and 64, respectively. The electro-optic modulator 40, rf signal generator 42, mixers 62 and 64, phase-compensating delay line 66 and 68, band pass filters 61 and 63, and low pass filters 69 and 71 provide the same type of FM derivative spectroscopy as employed with the non-relativistic beam of FIG. 1, resulting in demodulated outputs from mixers 62 and 64 which represent the derivatives of their respective photodiode input signals.

The outputs of mixers 62 and 64 are filtered in filters 69 and 71, respectively, and then delivered respectively to zero detector circuits 70 and 72, which sense the derivative signals crossing zero. The zero detector outputs are fed to a comparator/calculator circuit 74, which compares the laser frequencies at which the derivative signals cross zero and thereby calculates the atomic beam direction.

The two laser beams 46 and 48 should intersect the reference atomic beam axis 56 at equal angles $\alpha_1$ and $\alpha_2$. With the laser beams initially set to a Doppler shifted atomic resonance frequency of the atomic beam, a portion of the light from each laser beam will be resonantly absorbed by the atomic beam, with the remaining laser light detected by photodiodes 58 and 60. The two side bands of the laser beams will be absorbed differently, depending on how far the laser carrier signal is from the center of resonance. If the carrier is exactly on resonance, the two side bands will be absorbed equally. The signals from the side bands beating against the carrier frequency in the photodiode detectors 58 and 60 will then sum to zero, since the side bands are 180° out of phase with each other. If the laser carrier is to one side of the resonance, one side band will be absorbed more than the other, and the net beat signal from the side bands beating against the carrier will then be non-zero. Whether the carrier is above or below resonance can be determined from the phase of the rf beat signal.

The outputs of photodetectors 58 and 60 are phase-matched by inserting an appropriate delay with delay lines 66 and 68, and are demodulated in the rf mixers. Alternately, delay lines 66 and 68 could be placed between detectors 58, 60 and mixers 62, 64; phase shifters could be used instead of delay lines. The filtered DC mixer outputs will be the derivative, with respect to frequency, of the resonance profile for the atomic beam.

In the embodiment of FIG. 4, the atomic beam direction is determined by holding the angles of laser beams 46 and 48 constant relative to the reference axis, while the laser frequency is scanned. In another embodiment to be described, the direction of the relativistic atomic beam is determined by holding the laser frequency constant while varying the angles of the laser beams. If the laser beam angles are held fixed, the difference between the resonance frequencies of the two laser beams will be twice the frequency offset relative to the resonant frequency when the atomic beam is aligned with its reference axis. If the laser frequency is held fixed, the difference between the resonance angles of the two laser beams will be twice the angular offset of the atomic beam relative to its reference axis. In either case, the actual atomic beam direction is directly measured from the interval between the two resonance points.

Figure 5:
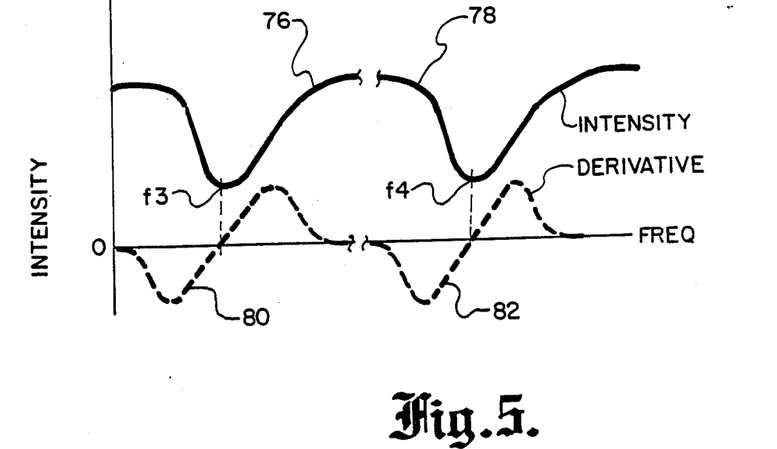
FIG. 5 is a graph of the individual laser beam intensities obtained with the system of FIG. 4 over the laser frequency spectrum, and the derivatives thereof, illustrating how the atomic beam direction is obtained from the two intensity profiles.

The DC components of the laser signals detected by photodiodes 58 and 60 are indicated by curve segments 76 and 78 in FIG. 5, while their respective derivatives, which are proportional to the filtered outputs of mixers 62 and 64, are indicated by dashed line curve segments 80 and 82. The various curve segments are plotted against frequency over the tunable frequency range of laser 38. When the aotmic beam is offset from its reference axis by a non-zero angle, one laser beam will experience resonant absorption by the atomic beam at one frequency $f_3$, while the other laser beam will be resonantly absorbed by the atomic beam at a different frequency $f_4$. Hence the laser beams are partially absorbed by the atomic beam at their respective resonant frequencies, and the laser beam intensity curves exhibit a dip or inverted peak at $f_3$ and $f_4$. The center of each inverted peak can be accurately determined by the zero crossing of its corresponding derivative curve.

The following expression has been determined to relate the angular offset $\delta$ between the atomic beam and the difference between the resonant laser frequencies $f_3$ and $f_4$:

$$\beta = \text{arc cosine } [(f_4 - f_3)/(2\gamma \nu \beta \sin \theta)],$$

where $\beta$ is the atomic beam velocity divided by the speed of light, $\gamma = (1 - \beta^2)^{0.5}$, $\nu$ is the frequency of atomic resonance in the rest frame of the atomic beam atoms (the resonance frequency seen by the moving beam atomics), and $\theta$ is the angle between the laser beams and a perpendicular to the reference atomic beam axis. Thus, given a measured frequency interval $f_4 - f_3$, the angle $\beta$ is precisely determined.

The angles $\alpha_1$ and $\alpha_2$ between the laser beams and a perpendicular to the reference atomic beam axis are normally selected to minimize the width of each inverted centroid in the laser intensity-frequency curve, and thereby enhance the measurement accuracy. The desired angle $\theta_m$ for both laser beams can be calculated from:

$$\theta_m = -\text{arcsine }(\beta),\text{ where }\beta\text{ is equal to the atomic beam velocity divided by the speed of light. For a 250 MeV H atomic beam, }\theta_m\text{ would be }-38°.\text{ To be resonant with the }H_\alpha\text{ transition in the rest frame of the atomic, the laser wavelength would need to be 519 nm.}$$

For the above desired value of $\theta_m$, the change in the resonant frequency resulting from a small change in the angle between the laser and atomic beams may be calculated to be 350 MHz/microradian, for the parameters given above. By comparison, the change in the resonance frequency resulting from an increase of one part in $10^4$ in the momentum of the atomic beam is 10.3 GHz, or about 30 times the angular frequency shift.

In some cases, it may be desirable to be slightly off from the angle $\theta_m$ that will produce the absolute narrowest inverted peak, in order to take advantage of the stability and reliability of single line lasers. In this case, the width of the inverted peaks will be somewhat greater, and the value of the FM derivative spectroscopy technique even greater.

Figure 6:
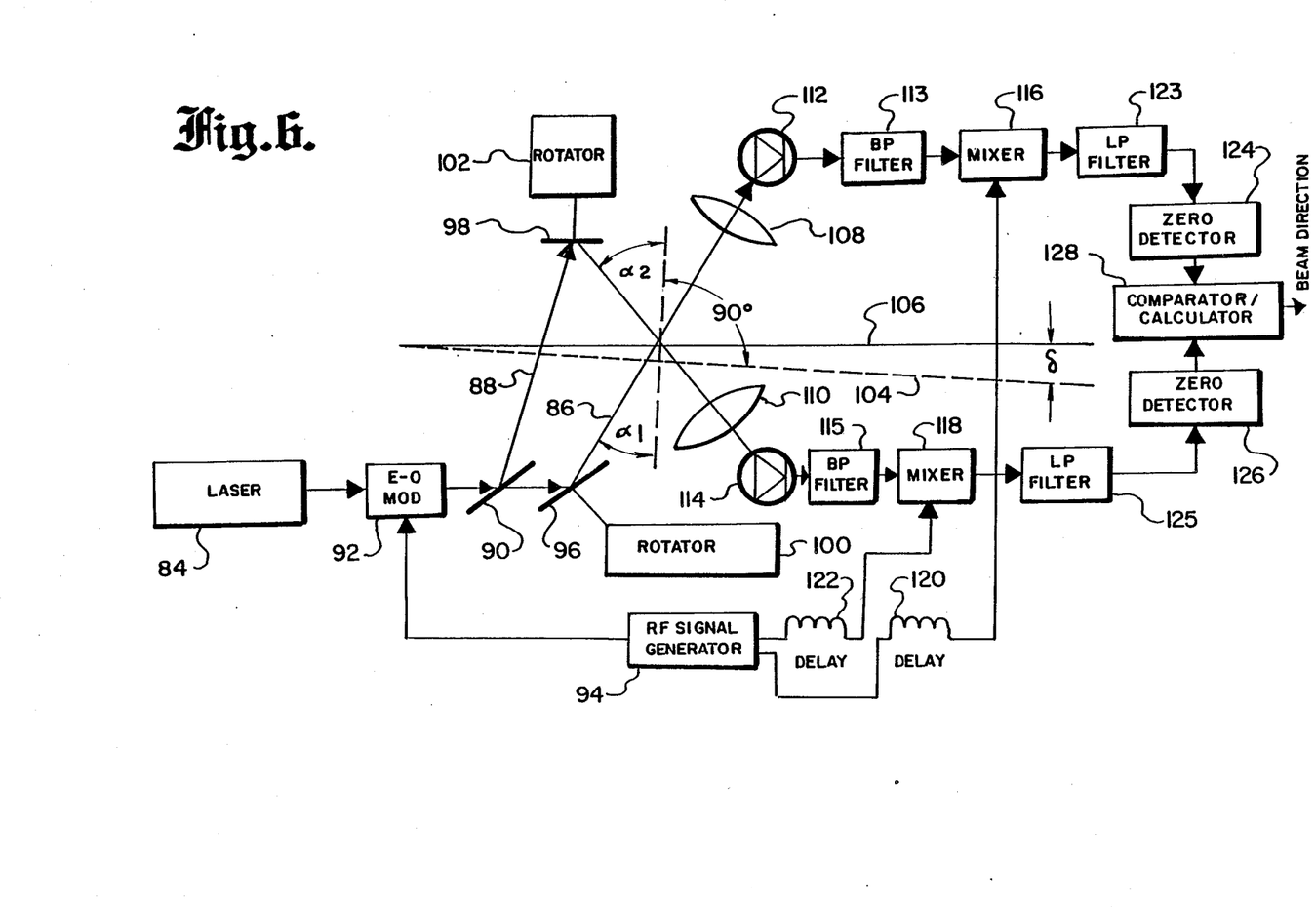
FIG. 6 is a block diagram of another embodiment of the invention intended for use with relativistic beams, in which the laser beam angles are varied while their frequency is held constant.

FIG. 6 illustrates the other embodiment referred to previously for a relativistic beam, in which the laser frequency is held fixed while the laser angle is tuned relative to the atomic beam. A fixed frequency laser 84 emits a beam which is split into beams 86 and 88 by a beam splitter 90. The laser beam is phase modulated by an electro-optic modulator 92 under the control of rf signal generator 94 to permit FM derivative spectroscopy, as in the previous embodiments. The sub-beams 86 and 88 are directed respectively to rotatable mirrors 96 and 98, the angular positions of which are respectively controlled by rotators 100 and 102. The two rotators are coordinated to rotate their respective mirrors about axes which are at right angles to the plane of the page, such that angles $\alpha_1$ and $\alpha_2$ between the reference axis 104 of atomic beam 106 an the laser beams 86 and 88, respectively, are known. The rotators consist of piezo-electric transducers whose angular tilts have been calibrated interferometrically.

The reflected laser beams 86 and 88 intersect the atomic beam from opposite sides, and are then focused by lenses 108 and 110 onto photodiodes 112 and 114, respectively. The lenses are large enough to focus the laser beams onto their respective photodetectors over the full range of angular variation. The outputs of photodiodes 112 and 114 are fed respectively through band pass filters 113 and 115 into mixers 116 and 118, which receive second inputs from rf signal generator 94 through delay lines 120 and 122, respectively. The photodiode outputs are demodulated in the rf mixers, whose DC outputs represent the derivatives of the laser beam intensities with respect to laser beam angle. After passage through low pass filters 123 and 125, zero crossings of the derivative signals from mixers 116 and 118 are observed by zero detectors 124 and 126, respectively. The zero crossings are compared and the atomic beam angular deviation from its reference axis determined by comparator/calculator circuit 128.

Figure 7:
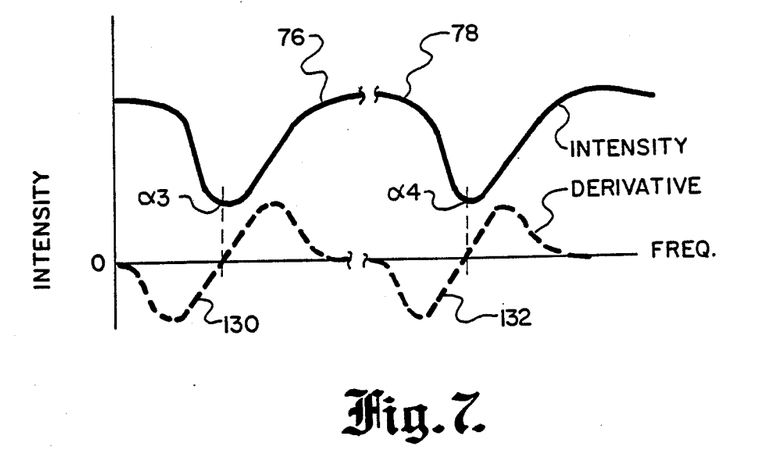
FIG. 7 is a graph of the laser beam intensity profiles and their derivatives, as a function of laser beam angle, for the system of FIG. 6.

An illustrative graph of the laser beam intensities detected by photodiodes 112 and 114, and of the derivative values produced by mixers 116 and 118, is given in FIG. 7 as a function of laser beam angle $\theta$. An angular profile similar to the frequency profile of FIG. 5 is observed. The intensity curve exhibits a pair of inverted peaks at angles $\alpha_3$ and $\alpha_4$, corresponding to the angles at which each of the laser beams establish a resonance with the atomic beam and are partially absorbed thereby. Zero crossings are obtained from the corresponding sections 130 and 132 of the derivative curve. The difference between the resonance angles $\alpha_3$ and $\alpha_4$ of the two laser beams is equal to twice the angular offset of the atomic beam relative to the reference axis.

In each of the embodiments described above, the atomic beam angle relative to the reference axis is determined in the plane of the two laser beams. The atomic beam's angular deviation in other planes can be obtained simply by providing redundant laser beams and sensing apparatus in those planes.

Laser sensing of the atomic beam direction is nonintrusive, senses the main beam direction, is easy to calibrate, measures direction independently of the beam position, is fast and easy to interpret, does not require a detailed knowledge of the optics used in the atomic beam accelerator, and can be accomplished over a comparatively short distance. Also, the described FM derivative spectroscopy technique is relatively insensitive to fluctuations or uncertainties in the atomic beam energy, and provides an error signal that is easy to integrate into a beam steering loop. With the disclosed relativistic beam sensing systems, the first order sensitivity to beam energy fluctuations and drifts is eliminated. Since the atomic beam direction is determined by taking the difference between two resonant frequencies or angles, the shifts introduced in both laser beams by drifts in the atomic beam momentum cancel each other. The result is a more accurate and reliable direction sensing for the atomic beam than has previously been obtainable.

While particular embodiments of the invention have been shown and described, it should be understood that numerous variations and alternate embodiments will occur to those skilled in the art. Accordingly, it is intended that the invention be limited only in terms of the appended claims.

We claim:

1. A system for measuring the angle between an atomic beam and a reference axis for the beam, comprising:

means for generating and directing a pair of laser beams having the same frequency through the atomic beam at known angles to the reference axis, means for varying a characteristic of the two laser beams, the varied characteristic being selected from the laser beam frequencies and their angles relative to the atomic beam, means for sensing the laser beam intensities as said characteristic is varied, means for obtaining the derivatives of the sensed laser beam intensities, and means for measuring the interval over the varying laser beam characteristic between the derivatives crossing zero as an indication of the angular deviation between the actual atomic beam axis and the laser beams, and thereby of the angular deviation between the actual beam axis and the reference axis.

2. The system of claim 1, wherein the directing means direct the laser beams as mutually counterpropagating beams, the means for varying varies the laser beam frequency, and said beam intensities sensing means is capable of sensing the combined intensity of the counterpropagating beams.

3. The system of claim 1, wherein the directing means direct the laser beams to be mutually angularly convergent upon the atomic beam from different sides of the beam, the beam intensities sensing means is capable of sensing the intensity of each laser beam individually, and the measuring means is capable of measuring the interval between the derivatives of the sensed intensities for the two beams crossing zero.

4. The system of claim 3, wherein the means for varying varies the laser beam frequencies, the means for varying said frequencies comprises a radio frequency signal generator and an electro-optic modulator which applies a radio frequency modulation from the signal generator to the two laser beams before they reach the atomic beam, the laser beam intensities sensing means comprises, for each laser beam, a photodetector positioned to sense the laser beam after transit through the atomic beam, and the means for obtaining the derivative of the sensed laser beam intensities comprises, for each laser beam, a radio frequency mixer connected in circuit with the photodetector and the signal generator to demodulate the photodetector output.

5. The system of claim 4, wherein one of the inputs to the mixer associated with each laser beam is connected to the mixer through a delay line selected to match the phases of the photodetector and signal generator inputs to the mixer.

6. A system for measuring the angle between an atomic beam and a reference axis for the beam, comprising:

means for generating and directing a pair of laser beams with a common frequency to intersect the atomic beam at known angles to the reference axis from different sides of the atomic beam, means for varying a characteristic of the two laser beams, the varied characteristic being selected from the laser beam frequencies and their angles relative to the atomic beam, means for sensing the individual laser beam intensities as said characteristic is varied, and means for measuring the interval over the varying laser beam characteristic between inverted peaks in the sensed laser beam intensities as an indication of the angular deviation between the actual atomic beam axis and the laser beams, and thereby of the angular deviation between the actual beam axis and the reference axis.

7. The system of claim 6, wherein the means for varying varies the laser beam frequencies and the directing means direct the laser beams at substantially equal angles to the reference axis.

8. The system of claim 6, wherein the directing means direct the laser beams at an angle to a perpendicular to the reference atomic beam axis whose sine is $(-\beta)$, where $\beta$ is the velocity of the atoms in the atomic beam divided by the speed of light.

9. The system of claim 6, wherein the directing means direct the laser beams to intersect at the atomic beam.

10. The system of claim 6, wherein the means for varying varies the laser beam angles relative to the reference beam axis, and the laser beam intensities sensing means comprises, for each laser beam, a photodetector and a lens positioned to focus the laser beam onto the detector, the lens being large enough to accommodate the angular variations in the laser beam.

11. The system of claim 6, wherein the means for varying varies the laser beam frequencies, the means for varying said frequencies comprises a radio frequency sweep signal generator and an electro-optic modulator which applies a radio frequency modulation from the signal generator to the two laser beams before they reach the atomic beam, and the measuring means includes means for demodulating the outputs of the laser beam intensities sensing means.

12. The system of claim 6, said measuring means comprising means for obtaining the derivatives of the sensed laser beam intensities, and means for measuring the interval over the varying laser beam characteristic between the derivatives crossing zero.

13. A method of measuring in real time the angle between an atomic beam and a reference axis for the beam, comprising:

generating a pair of laser beams with a common frequency, counterpropagating the laser beams through the atomic beam at a known angle to the reference axis, varying the frequencies of the laser beams in coordination with each other, sensing the laser beam intensities as their frequencies are varied, and measuring the frequency interval between peaks in the sensed laser beam intensities as an indication of the angular deviation between the actual beam axis and the reference axis, with the proviso that the angular deviation is not approximately 90°.

14. The method of claim 13, wherein the laser beam intensities are sensed by sensing light scattered from the laser beams as a result of interaction with the atomic beam.

15. The method of claim 13, wherein the laser beams are directed at substantially right angles to the reference atomic beam axis.

16. A method for measuring the angle between an atomic beam and a reference axis for the beam, comprising:

generating a pair of laser beams with a common frequency, directing the laser beams through the atomic beam at known angles to the reference axis, varying a characteristic of the laser beams which is selected from the laser beam frequencies and their angles relative to the atomic beam, sensing the laser beam intensities as said characteristic is varied, obtaining the derivatives of the sensed laser beam intensities, and measuring the interval over the varying laser beam characteristic between the derivatives crossing zero as an indication of the angular deviation between the actual and reference atomic beam intensities.

17. The method of claim 16, wherein the laser beams are directed as mutually counterpropagating beams, the varied characteristic is the laser beam frequency, and the joint intensity of the counterpropagating beams is sensed.

18. The method of claim 16, wherein the laser beams are directed to be mutually convergent upon the atomic beam from different sides of the beam, the intensity of each laser beam sensed individually, and the interval between the derivatives of the sensed intensities for the two beams crossing zero is measured.

19. A method for measuring the angle between an atomic beam and a reference axis for the beam, comprising:

generating a pair of laser beams with a common frequency, directing the laser beams to intersect the atomic beam at known angles to the reference axis from different sides of the atomic beam, varying a characteristic of the laser beams which is selected from the laser beam frequencies and their angles relative to the atomic beam, sensing the individual laser beam intensities as said characteristic is varied, and measuring the interval over the varying laser beam characteristic between inverted peaks in the sensed beam intensities as an indication of the angular deviation between the actual beam axis and the reference axis.

20. The method of claim 19, wherein the laser beam frequencies are varied and the laser beams are directed at substantially equal angles to the reference axis.

21. The method of claim 19, wherein the laser beams are directed at an angle to a perpendicular to the reference atomic beam axis whose sine is $(-\beta)$, where $\beta$ is the atomic beam velocity divided by the speed of light.

22. The method of claim 19, wherein the laser beams are directed to intersect at the atomic beam.

* * * * *

UNITED STATES PATENT AND TRADEMARK OFFICE
CERTIFICATE OF CORRECTION

PATENT NO. : 4,797,552

DATED : January 10, 1989

INVENTOR(S) : Duncan G. Steel et al

It is certified that error appears in the above-identified patent and that said Letters Patent is hereby corrected as shown below:

Col. 8, line 27, delete the first " $\beta$ " and insert therefor -- $\delta$ --.

Signed and Sealed this

Sixth Day of June, 1989

Attest:

DONALD J. QUIGG

Attesting Officer

Commissioner of Patents and Trademarks